United States Patent [19]

Matkovich et al.

[11] Patent Number: 5,151,192
[45] Date of Patent: Sep. 29, 1992

[54] METHOD FOR REMOVING HEPARIN FROM BLOOD OR PLASMA

[75] Inventors: Vlado I. Matkovich, Glen Cove; Peter J. Degen, Huntington; Thomas C. Gsell, Glen Cove; Thomas Bormann, Seaford; Isaac Rothman, Brooklyn, all of N.Y.

[73] Assignee: Pall Corporation, Glen Cove, N.Y.

[21] Appl. No.: 552,138

[22] Filed: Jul. 13, 1990

[51] Int. Cl.⁵ .................. B01D 61/00; B01D 15/00
[52] U.S. Cl. .................. 210/646; 210/651; 210/679; 210/690; 210/691; 210/692; 436/177; 436/178; 536/21; 604/4; 604/5
[58] Field of Search .......... 210/638, 651, 679, 690, 210/691, 692, 807, 321.6, 502.1, 490, 491, 496, 506, 508, 500.27, 500.35, 500.37, 500.38, 646; 604/4, 5; 536/21; 436/177, 178

[56] References Cited

U.S. PATENT DOCUMENTS

| | | |
|---|---|---|
| 3,099,600 | 7/1963 | Toccaceli . |
| 3,337,409 | 8/1967 | Williams . |
| 4,198,314 | 4/1980 | Butler et al. ............ 252/427 |
| 4,199,502 | 4/1980 | Babson et al. ............ 260/121 |
| 4,226,599 | 10/1980 | Butler et al. ............ 536/21 |
| 4,439,322 | 3/1984 | Sonoda et al. ............ 210/500.35 |
| 4,473,474 | 9/1984 | Ostreicher et al. ............ 210/636 |
| 4,702,840 | 10/1987 | Degen et al. ............ 210/638 |
| 4,707,266 | 11/1987 | Degen et al. ............ 210/638 |
| 4,906,374 | 3/1990 | Gsell ............ 210/500.38 |
| 4,935,204 | 6/1990 | Seidel et al. ............ 424/101 |
| 4,936,998 | 6/1990 | Nishimura et al. ............ 210/638 |
| 5,000,854 | 3/1991 | Yang ............ 210/638 |

FOREIGN PATENT DOCUMENTS

| | | |
|---|---|---|
| 0077633 | 4/1983 | European Pat. Off. . |
| 0219053 | 4/1987 | European Pat. Off. . |
| 0281128 | 9/1988 | European Pat. Off. . |
| 2921924 | 12/1980 | Fed. Rep. of Germany . |
| 2016943 | 10/1979 | United Kingdom . |
| 2135207 | 8/1984 | United Kingdom . |

OTHER PUBLICATIONS

Koich et al., "Experimental Study on the Adsorption of Excess Heparin with Anion Exchange Resin Fiber", Chemical Abstracts, 1989, pp. 425–426.

Primary Examiner—Robert A. Dawson
Assistant Examiner—Sun Uk Kim
Attorney, Agent, or Firm—Leydig, Voit & Mayer

[57] ABSTRACT

A porous medium having a positive surface change removes heparin from a heparin-containing liquid, without removing other proteinaceous components from the liquid. Methods and devices are disclosed.

39 Claims, No Drawings

METHOD FOR REMOVING HEPARIN FROM BLOOD OR PLASMA

TECHNICAL FIELD

This invention relates to a method and a device for removing heparin from a blood sample, particularly whole blood or blood plasma. This invention also relates to a method for rapidly deheparinizing blood in order to enable clinical diagnoses based on blood coagulation factors. The invention may also be used diagnostically to detect the presence of heparin.

BACKGROUND OF THE INVENTION

Heparin and other natural and artificial acid polysaccharides or mucosaccharides are polyanions which exhibit anticoagulant properties, and are often used therapeutically to reduce or prevent coagulation of a patient's blood.

Blood coagulation or clotting is the precipitation of fibrin from blood or plasma, and depends, in part, on a complex cascade of plasma proteins (factors). Some of these blood coagulation factors are routinely used as an indicator of a patient's clinical condition or of a patient's response to therapeutic drugs.

The primary coagulation assays, prothrombin times (PT) and activated partial thromboplastin times (aPTT), measure the amount of time required for the formation of the first filament of fibrin. The presence of heparin, however, artificially increases the PT and aPTT, thus reducing the accuracy of the coagulation assays, thereby providing a false indication of the patient's clinical condition. It is, therefore, very desirable to determine the accurate coagulation parameters of a patient's blood independent of therapeutic or incidental heparin levels. In order to do this, heparin in the sample of the patient's blood must be efficiently removed (or neutralized), before the coagulation parameters are assayed. Practitioners routinely remove or identify heparin using methods such as protamine neutralization, resin absorption, or thrombin/reptilase times, but these methods may be time consuming, cumbersome, and expensive.

In protamine neutralization, for example, a precisely determined dosage of protamine sulfate (a low molecular weight fish polypeptide extract) is typically used. The dosage is generally calculated based on a ratio of one mg of protamine neutralizing 90 units of lung heparin or 115 units of intestinal heparin. In cardiothoracic surgery, for example, 150–300 mg of protamine may be required. Determining the proper dosage requires the utmost precision because protamine, and other neutralizing agents such as polybrene, are soluble in plasma. Any excess neutralizing agent not combined with heparin will remain in the plasma and may interfere with the coagulation test.

Furthermore, the number and noxiousness of protamine sulfate's side effects exacerbates the inherent risks associated with its use, and may contribute to a patient's morbidity and/or mortality. Common side effects include decreased peripheral vascular resistance, vasodilation, hypotension, decreased cardiac output, dyspnea, increased or decreased pulmonary arterial resistance, decreased arterial $PO_2$, bleeding, or complement activation (via the heparin-protamine complex). In patients connected to an extracorporeal circuit, the major adverse reactions may include immediate anaphylactic shock (an antibody-mediated allergic reaction which is not dose-dependent) or a delayed response characterized by noncardiogenic pulmonary edema or persistent hypotension (which probably is dose dependent).

An alternative to protamine neutralization is the removal of heparin from the blood, typically by the addition of a heparin complexing agent. Two means for removing heparin from blood plasma are available commercially. One, the Probe-Tek Heparin Adsorbent, manufactured by Probe-Tek, Inc., is a cationic modified cellulose which is supplied as a premeasured dose of heparin adsorbent in a tube, to which 1 ml blood plasma is added. After gently mixing and standing for one minute, the plasma with the adsorbent is centrifuged at 1500 times the force of gravity for 10 minutes. The supernatant is then carefully removed from the tube with a pipette, and used for testing.

The second means, Hepasorb ®, is manufactured by Organon Teknika Corporation and is a cellulose which has been modified to contain quaternary ammonium groups. Hepasorb (70 mg) is added to a test tube, and is agitated gently with 1 ml blood plasma for about 10 seconds. It is cautioned that prolonged agitation can cause denaturation of the plasma proteins. After agitation the tube must be mixed slowly for 10 minutes at room temperature and centrifuged for 5 minutes at 12000 times the force of gravity. The supernatant is then withdrawn from the centrifuge tube for testing.

All of these methods and products for removing heparin from a blood sample are difficult and time-consuming, require specialized equipment, require about 20 minutes for even an experienced laboratory worker to prepare a single sample of plasma for testing, require extreme care in the removal of the supernatant plasma after centrifuging to prevent contamination of the deheparinized plasma with adsorbent, and do not completely solve the need articulated by practitioners in the art.

For example, during surgery, the majority of deleterious reactions due to the presence of protamine occur immediately (i.e., they are not dose dependent). A filter for removing substantially all of the heparin typically used (about 15,000–30,000 units) would be most desirable, particularly if the filter could achieve a flow rate of about 2.5–6 liters/minute (for hemo-diluted patients) and have a priming volume of about 200–225 ml. Such a filter would eliminate the need for pre-operative testing to determine a patient's prior sensitization, would eliminate protamine's adverse side effects which may lead to morbidity and/or death, and would reduce time and costs associated with adverse protamine reactions.

SUMMARY OF THE INVENTION

It has been found that a porous medium having controlled surface properties can remove heparin from blood or plasma without removing therapeutically or clinically significant amounts of blood clotting factors. Porous media suitable for use according to the invention have a positive surface charge in aqueous solution. It has also been found that when the medium has been surface modified to provide a positive surface charge, it is possible to remove heparin from a blood sample, without removing a significant amount of blood clotting factors, simply by contacting the blood sample with the surface-modified medium. It has also been found that the required residence time is typically very short (e.g. as little as fractions of a second), thus permitting the efficient removal or detection of heparin in a blood sample. Furthermore, heparin can be removed from blood or plasma by contact with a medium of the present invention without the need for pre-filtration, or pretreatment with buffers or pH controllers. In this manner, heparin may be removed from a blood sample without adversely affecting subsequent testing of the blood sample for clotting time. Thus, the heparin-free sample may then be subjected to coagulation tests in order to determine true clotting time.

DESCRIPTION OF THE EMBODIMENTS

A porous medium in accordance with the invention comprises a porous medium having a positive surface charge, which removes a clinically significant amount of heparin from a heparin-containing liquid, such as blood, without removing other proteinaceous components from the liquid, wherein the positive surface charge preferably comprises amino groups and/or quaternary ammonium groups on the surface of the porous medium. Porous medium, as used herein, refers to a self-supporting or non-self-supporting polymeric fibrous matrix, polymeric membrane, or a rigid porous medium. Self-supporting, as used herein, refers to structures which have structural integrity, e.g., a fibrous matrix comprised of mechanically entangled fibers which maintains its unitary structure and its porous nature under intended conditions of use; that is, the structure is resistant to compressive or deformation forces. Such structures are more readily produced, handled, and transported. Additionally, the likelihood of media migration, i.e., the undesirable sloughing off of small particles of the medium which are then carried through the filter and into the downstream filtered product, is reduced with such self-supporting structures. Further, the self-supporting structures of the present invention substantially retain the inherent adsorption characteristics of the medium with minimal increase in pressure drop across the structure, as compared to similar non-immobilized particles or non-self-supporting structures. Heparin-containing liquid, as used herein, refers to a fluid which contains heparin, such as blood or plasma. Blood, as used herein refers to whole blood; treated blood, such as blood diluted with a physiological solution; and one or more blood components, such as packed red cells. In an embodiment of the invention, the porous medium is self-supporting; in another embodiment of the invention, the porous medium may be either self-supporting or non-self-supporting and is disposed in a housing, such as a syringe or an extracorporeal filter.

As used herein, "without substantial removal of blood clotting factors" means that the porous media of the invention remove heparin without removing other blood components which affect blood clotting, such as Factor IX, in amounts which adversely affect the accuracy of diagnostic tests, such as blood clotting tests. Porous media according to the present invention preferably exhibit a relatively low binding affinity for proteinaceous components of the blood. However, zero removal of proteinaceous blood components is not required. Also, the porous media preferably should not cause any detectable blood hemolysis, although for the purposes of some diagnostic tests, a small degree of hemolysis may be tolerated without significantly affecting the test.

In accordance with an embodiment of the invention, a porous medium having a positive surface charge comprises amino and/or ammonium groups, particularly quaternary ammonium groups, on the surface of the medium in an amount sufficient to remove heparin from a blood sample. The presence of amino and/or ammonium groups on the surface of the medium provides the positive surface charge, and contributes to the production of a positive zeta potential on the surface of the medium. Typically, the positive surface charge is obtained by at least one ethylenically unsaturated monomer containing pendant amino and/or ammonium groups.

The amino and/or ammonium groups may be present at the time of formation of the medium or they may be In accordance with an embodiment of the invention, the porous medium may comprise a substrate, surface-modified with a superstrate, for removing heparin from a blood sample. Substrate, as used herein, refers to a polymeric fiber (including hollow fibers), a polymeric fiber matrix, a polymeric membrane, or a solid porous medium. Superstrate, as used herein, refers to a layer of polymer formed at and substantially covering the surface of the substrate. Substantially covering the surface, as used herein, refers to the amount required to form a porous medium which removes heparin without removing blood clotting factors. A matrix, as the term is used herein, indicates a three-dimensional network of fibers, which together form a coherent self-supporting structure. The fibers themselves may be continuous, staple, or melt-blown. The fibers may be made from any material compatible with blood and may be treated in a variety of ways to make the medium even more effective. Also, the fibers may be bonded, fused, or otherwise fixed to one another or they may simply be mechanically entwined. A membrane, as the term is used herein, refers to one or more porous polymeric sheets, such as a woven or non-woven web of fibers, with or without a flexible porous substrate. The porous, polymeric sheet typically has a substantially uniform, continuous matrix structure containing millions of very small capillary pores.

In an embodiment of the invention, the surface of the substrate may be modified to include a polymer containing amino and/or ammonium groups, particularly quaternary ammonium groups, and is suitable for use in removing a clinically significant portion of heparin in a heparin-containing liquid, such as blood, which is passed through the medium.

The substrate of this invention may be formed, for example, from any synthetic polymer capable of forming fibers and of serving as a substrate for grafting with ethylenically unsaturated monomeric materials. Preferably, the polymer should be capable of reacting with at least one ethylenically unsaturated monomer under the influence of ionizing radiation without the matrix being adversely affected by the radiation. Suitable polymers for use as the substrate include, but are not limited to, polyolefins, polyesters, polyamides, polysulfones, polyarylene oxides and sulfides, and polymers and copolymers made from halogenated olefins and unsaturated nitriles. Preferred polymers are polyolefins, polyesters, and polyamides. The most preferred polymer is polybutylene terephthalate (PBT).

Preferred substrates may include ethylenically unsaturated monomers which yield an amino or ammonium group incorporated into the grafted polymer by means of a non-hydrolyzable linkage. This enables the product to better withstand certain environments, such as prolonged exposure to hot water and alkaline or acidic conditions, without substantial loss of the product's surface qualities. Further, the substrate may be configured into any geometric shape suitable for use as a porous medium, including but not limited to a web, a sheet, a solid body such as a disk or cylinder, or a hollow body such as a hollow cylinder; the porous medium may include additional structures such as end caps, edge seals, a cage, a core, or a wrap. The medium preferably comprises a depth filter, which preferably comprises a mass of fibers, and more preferably, a mass of microfibers.

In accordance with an embodiment of the invention, the substrate may be treated or modified in order to form a substrate having a modifying agent or superstrate thereon. In accordance with an embodiment of the invention, the substrate may be modified to form a superstrate comprising a polymer derived from at least one ethylenically unsaturated monomer containing pendant amino and/or ammonium groups, particularly quaternary ammonium groups. In a preferred embodiment, the medium is modified in such a manner that the surface properties of the medium are controlled by the modifying agent such that the underlying structure does not adversely effect the blood sample's coagulation properties. Examples of ethylenically unsaturated monomers containing pendant quaternary ammonium groups include but are not limited to polymerizable ethylenically unsaturated monomers which either contain an ammonium group or a functionality which is capable of being converted to an ammonium group. For example, the monomer may contain primary, secondary or tertiary amino groups, and then any primary, secondary or tertiary amine groups in the grafted superstrate may be quaternized in situ. Suitable monomers include, but are not limited to the quaternized derivatives of aminoalkyl acrylates and methacrylates, such as the methochlorides of dimethylaminoethyl acrylate or methacrylate; quaternized aminoalkyl acrylamides and methacrylamides, such as MAPTAC (methacrylamidopropyltrimethylammonium chloride); styrenic compounds, such as the methochloride of dimethylaminostyrene; and vinylic compounds such as dimethyldiallylammonium chloride (DMDAC). If the monomer has pendant quaternary ammonium groups, the most preferred monomer is trimethyl ammonium ethyl acrylic chloride (TMAEAC). If the monomer has pendant amino groups, the most preferred monomer is diethylamino ethyl methacrylate.

The presence of amino and/or quaternary ammonium groups on the surface of the substrate provides the positive surface charge, and contributes to the production of a positive zeta potential on the surface of the substrate. Amino and/or quaternary ammonium groups may be present at the time of formation of the superstrate or they may be introduced after the superstrate is first formed. Fiber-forming polymers tend to have strong negative zeta potentials. In addition, certain fiber forming processes, such as melt spinning or melt blowing, create negatively charged functionalities (such as carboxyl groups) on the fiber surface. Such groups enhance the already strong negative zeta potential of the polymer. On the other hand, in a preferred embodiment, quaternary ammonium groups, because they bear a full, permanent positive charge, neutralize and overcome the negative zeta potential of the substrate polymer surface. In another embodiment, unquaternized (free) primary, secondary or tertiary amino groups are capable of being protonated in aqueous systems and bear a positive charge. The amount of positive charge may be sufficient to overcome the strong negative potential of some polymeric fiber materials, and thus, may be capable of removing heparin.

In an embodiment of the invention, the superstrate may also include at least one other monomer in combination with the amino and/or ammonium group-containing monomer. These other monomers may be completely inert or may contain functional groups which confer additional desired properties or exercise control over the surface properties already conferred by the amino or ammonium group-containing monomers, provided that the additional monomers do not also contain functional groups which interfere with the formation of the grafted porous medium. Suitable monomers include polar, non-ionic, ethylenically unsaturated monomers. The polar monomer may promote hydrogen-bonding, may contain more than one polymerizable ethylenically unsaturated group, and/or may impart hydrophilicity to the porous medium. When such monomers are incorporated into the grafted superstrate, the superstrate may become cross-linked. A cross-linked superstrate is more resistant to change in its molecular conformation and, as a result, provides a fiber matrix whose surface properties are less affected by the chemical environment or heat. Certain monomers which contain both conjugated and non-conjugated polymerizable double bond systems, such as allyl methacrylate (AMA), are particularly effective. These appear to increase the efficiency of grafting the superstrate to the substrate surfaces. The presence of monomers which have more than one polymerizable ethylenically unsaturated group can be beneficial in another respect. For unknown reasons, the treatment of large, non-uniform shaped fiber matrices sometimes results in a matrix in which the surfaces are not treated uniformly; non-uniform treatment may result in local variation in filtration capabilities within the porous medium.

Such polar, non-ionic monomers include but are not limited to, polymethacrylate and polyacrylate esters of polyols, such as diethylene glycol dimethacrylate (DEGDMA) and pentaerithritol triacrylate; acrylate and methacrylate esters of ethylenically unsaturated alcohols, such as AMA; hydroxyl-containing monomers including hydroxylalkyl acrylates, such as hydroxypropyl acrylate (HPA) and methacrylates, such as hydroxyethyl methacrylate (HEMA); and materials such as triallyl trimellitate, divinylbenzene and other small monomers having more than one polymerizable ethylenically unsaturated functional group. If the positive surface charge is provided by a monomer containing pendant ammonium groups, the most preferred non-ionic monomer is diethylene glycol dimethacrylate (DEGDMA). If the positive surface charge is provided by a monomer containing pendant amino groups, the most preferred non-ionic monomer is methyl methacrylate. The inclusion of a monomer having a hydrophobic moiety, such as methyl methacrylate, may also be used to obtain precise control over the final hydrophilicity of the matrix by modifying the effect of monomers conferring hydrophilic characteristics.

In accordance with an embodiment of the invention, porous media of the invention can be produced from a pre-existing substrate by a process comprising the graft polymerization of the superstrate onto the surface of the substrate. Alternatively, in an embodiment of the invention, the superstrate may be grafted onto the surface of individual fibers prior to the fibers being formed into a matrix, membrane, or rigid porous medium.

A porous medium of this invention is preferably formed by contacting a substrate, either as a preexisting matrix or as individual fibers prior to their formation into the matrix, with a grafting solution comprising the superstrate in a suitable solvent, and exposing the substrate to ionizing radiation under conditions which polymerize the superstrate and result in a filter medium having the desired surface properties. The monomers in the grafting solution preferably form a polymer bonded to the surface of the substrate fibers or fiber matrix. The term bonded, as used herein, refers to the superstrate being sufficiently attached to the substrate or to each other so that the superstrate will not significantly extract under the intended conditions of use.

When the superstrate comprises an amino and/or ammonium group-containing monomer in conjunction with a polar, hydrogen-bonding, non-ionic, polymerizable, ethylenically unsaturated monomer, the amino and/or ammonium group-containing monomer may be present in the grafting solution in an amount typically ranging from about 0.1% to about 10% by weight, and more preferably between about 0.20% and about 7% by weight. The more amenable the fibers of the matrix are to graft polymerization, the lower the concentration of monomer required to achieve the desired effect. Most preferred are monomer concentrations ranging from about 0.3% to about 5% by weight. The polar, hydrogen-bonding, non-ionic, polymerizable ethyenically unsaturated monomer may be present in an amount ranging from about 0.1% to about 10% by weight, more preferably from about 0.25% to about 5% by weight, and especially preferred are concentrations ranging from about 0.3% to about 2% by weight.

In accordance with the invention, however, it is only required that the grafted superstrate contain sufficient amino and/or quaternary ammonium groups to overcome the negative potential inherent at the substrate surface.

To form the grafting solution, the monomer(s) may be dissolved in any solvent or combination of solvents which is capable of dissolving all of the monomer(s) and which does not interfere with the formation of the polymer. For example, when amino or quaternary ammonium group-containing monomers are used together with HEMA and AMA, the preferred solvent is water. However, if monomers are used which are not fully soluble in water, an amount of a water-miscible inert organic solvent, such as 2-methylpropan-2-ol or a mixture of 75% deionized water and 25% tertiary butyl alcohol, may be added in an amount sufficient to enable complete dissolution of the monomers. Some nonaqueous solvents, however, may decrease the solubility of some quaternary ammonium group-containing monomers. Hence, non-aqueous solvents should not be added in an amount that renders the ammonium group-containing monomer insoluble.

The substrate, in the form of individual fibers, porous matrix, membrane, or shaped article, may be contacted with the coating solution by any appropriate means, including, but not limited to spraying, dipping, or vacuum impregnation. The amount of contact is preferably sufficient to substantially completely, and more preferably, to completely coat the surface of the substrate. If a large enough portion of the substrate is left uncovered, the porous medium may remove blood components (particularly Factor IX) in quantities that might effect the accuracy of a diagnostic blood clotting test, and therefore, may, under some circumstances, be undesirable.

If the substrate is easily wetted by the coating solution, it should be sufficient to pass the substrate through a bath of the coating solution. If the substrate is not easily wetted by the coating solution, mechanical means may be used to force the solution onto the fibers. For example, the fibers may be placed on a vacuum drum which will draw the coating solution onto the fibers.

Alternatively, the substrate may be placed in a container which is then sealed, evacuated, and then filled with superstrate solution. If this method is used, the superstrate solution should preferably be thoroughly degassed prior to being placed in the container.

Once the surface area of the substrate is saturated and preferably placed in contact with an excess amount of coating solution, the substrate is exposed to ionizing radiation. Gamma radiation is preferred, and gamma radiation from a $^{60}$Cobalt source is most preferred, although other sources of ionizing radiation may be used, provided that the radiation is capable of initiating graft polymerization. Irradiation at any dose rate is acceptable, provided substrate having the desired surface properties. Dose rates from about 1 to about 1,000 kilorads/hr and preferably from about 5 to about 100 kilorads/hr may be used. In general, higher dose rates may be typically required for substrates which appear to react poorly with the ammonium or amino group-containing monomer when no other comonomers are present. A dose rate of about 10 kilorads/hr for a total dose of about 0.2 Mrads is especially preferred for forming a superstrate from DMDAC, HEMA, and AMA on a PBT fiber matrix. Typically, total doses in the range of from about 0.05 to about 5 Megarads may be used.

After irradiation and formation of the positive charge on the surface of the substrate, the surface-modified substrate may be washed with water to remove any polymeric debris which is not bonded to the substrate. Any means of washing which causes water to flow across all the fibers, either loose or in a matrix, is appropriate, provided that it is sufficient to remove all of the unbound debris. For example, washing a fiber matrix is typically conducted by flowing deionized water through the matrix for about 5 hours at a flow rate of about ⅛ gallons per minute (gpm) for each 100 square inches of external surface area.

After washing, the surface-modified porous medium is dewatered and/or dried. Insufficient drying may result in the porous medium removing blood components other than heparin. Over-drying may cause embrittlement or other detrimental affects to the modified substrate. Typically, the porous medium may be dried at about 100° C. to about 120° C. for between about 24 hours and about 72 hours. In a preferred embodiment, the porous medium is dried at about 100° C. for about 72 hours.

While not intending to be restricted to a certain theory, it is believed that the porous medium in accordance with the present invention removes heparin from a heparin-containing liquid by means of adsorption rather than by mechanical removal. Consequently, the total surface area of the porous media may be selected to optimize the properties of the device, depending on the specific application. As used herein, the term total surface refers not only to the gross or external surface(s) of the medium, but also to the internal surfaces of the medium which are contacted by fluid during use.

Typically, the porous media useful in the subject invention will have a total surface area ranging from about 0.01 $M^2/g$ to about 20 $M^2/g$, preferably from about 0.2 $M^2/g$ to about 10 $M^2/g$.

Because of the efficiency of a porous medium used as heparin adsorbent, only a small amount of the medium need be used. Therefore, the percent voids of the adsorbent may be as small as a few microliters to ensure that no significant amount of liquid is wasted by being held up in the adsorbent. Typically, the percent voids may be in the range from about 50% to about 95%.

Also because of the efficiency of porous media according to the present invention, the required average residence time of the fluid sample in the void space of a porous medium is minimal. Typically, the residence time may be in the range from about 0.1 second to about 50 seconds.

In accordance with a preferred embodiment of the invention, a blood sample is drawn into a syringe and forced by hand pressure through a modified matrix structure capable of adsorbing heparin, thereby removing the heparin from the plasma, if present. Preferably, about 1 ml plasma is forced through the modified matrix secured in a filter holder (device) for about 1 to 50 seconds preferably from about 1 to about 10 seconds. Typically, the porous medium of the present invention removes from about 1 to about 4 units of heparin for about every 1 square inch of media. The heparin-free plasma can be collected in a tube or vial for storage or can be expelled directly into cells or cuvettes commonly used in laboratory device for determining coagulation parameters.

Porous media in accordance with the invention may be configured in a device which can be attached to the end of a syringe. The liquid can then be expelled through the adsorbent into a suitable collection tube, thereby producing a heparin-free liquid. Alternatively, the absorbing medium can be configured in a device such that it can first be attached to a syringe. The free end of the device can be inserted into a liquid sample, and the liquid can be withdrawn through the absorbing medium into the syringe, thereby removing any heparin from the liquid. The device can then be removed from the end of the syringe and the deheparinized liquid can be expelled into a suitable collection tube. In a third embodiment, the absorbing medium can be configured in a device such that the device can be attached to the end of a syringe, the free end of the device can be immersed in a liquid sample and liquid can be withdrawn into the syringe through a check valve in the device, thereby bypassing the absorbing medium, and then be expelled through the absorbing medium into a suitable collection tube. In a fourth embodiment the device may be configured to be attached to the end of a syringe and immersed in a liquid sample. The liquid can then be withdrawn into the syringe through the absorbing medium and then be expelled using the syringe, bypassing the absorbing medium via a check valve, directly into a suitable collection tube. In a fifth embodiment, the porous medium may be incorporated into an extracorporeal circuit in, for example, an extracorporeal filter or dialysis filter.

For example, a typical syringe filter assembly may comprise a barrel syringe, a filter in accordance with the invention removably attached to one end of the syringe, and a "snorkel" or tip removably attached to the filter. The filter typically comprises a porous medium according to the invention in the form of a disc membrane encased within a housing having first and second fittings on opposite sides of the disc. The first fitting may be removably attached to the syringe, and the second fitting may be removably attached to the snorkel. The snorkel may comprise a flexible, semi-rigid or rigid cannula-like structure which is of a specific length so as to allow access to plasma in a standard vacutainer tube without allowing red cells to be drawn into the syringe. Typically, withdrawing the plunger of the syringe draws plasma sequentially into the snorkel, through the filter, and into the syringe. The surface area of the filter is large enough to allow plasma to flow easily through the filter with only the delta-p across the filter generated by a reasonably steady withdrawal of the plunger. A typical diameter of the membrane is about one inch. The snorkel and filter may then be discarded, and the filtered plasma in the syringe may be dispensed into a tube.

A typical filter assembly for use in an extracorporeal circuit comprises a housing, having an and an outlet, and a porous medium according to the invention disposed in the housing for the removal of heparin from the blood sample. The porous medium may have a disc-like or cylindrical shape and may be packed in the housing to contact liquid flowing longitudinally or axially through the filter element.

Any housing of suitable shape to provide an inlet and an outlet for a liquid and a space for a porous medium disposed between the inlet and outlet can be employed Housings can be designed in a variety of shapes. For example, a square or octagon shaped housing and other possible forms designed to accommodate a porous medium would in principle all be functional. These shapes are within the scope of the claimed invention.

General Procedure for Measuring Zeta Potential

Zeta potential was measured using a ½ inch diameter ×¼ inch thick cylindrical plug of fiber matrix, cut from the innermost ½ inch of a filter medium (nearest the core of the filter), or if a fibrous web, the sample was cut from a ½ inch thick stack of webs.

The zeta potential was measured by placing the sample in an acrylic filter holder which held the sample snugly between two platinum wire screens $100 \times 100$ mesh (i.e., 100 wires in each direction per inch). The meshes were connected, using copper wire, to the terminals of a Triplett Corporation model 3360 Volt-Ohm Meter, the mesh on the upstream side for the sample being connected to the positive terminal of the meter. A pH-buffered solution was passed through the sample using a differential pressure of 45 inches of water column across the filter holder and the effluent was collected. For measurements at pH 7, a buffered solution was made by adding 6 ml pH buffer (Fisher Scientific Co. catalog number SB108-500) and 5 ml pH 7.4 buffer (Fisher Scientific Co. catalog number SB110-500) to 1 liter pyrogen-free deionized water. For measurements at pH 9, a buffered solution was made by adding 6 ml pH 7 buffer (Fisher Scientific Co. catalog number SB114-500) and 2 ml pH 10 buffer (Fisher Scientific Co. catalog number SBl16-500) to 1 liter pyrogen-free deionized water. The electrical potential across the filter holder was measured during flow (it required about 30 seconds of flow for the potential to stabilize) and was corrected for cell polarization by subtracting from it the electrical potential measured when flow was stopped. During the period of flow the pH of the liquid was measured using a Cole-Parmer model J-5994-10 pH meter fitted with an in-line model J-5993-90 pH probe. The conductivity of the liquid was measured using a Cole-Parmer model J-1481-60 conductivity meter fitted with a model J-1481-66 conductivity flow cell. Then the polarity of the volt meter was reversed, and the effluent was flowed backwards through the filter holder using a differential pressure of 45 inches of water column. As in the first instance the electrical potential measured during flow was corrected for cell polarization by subtracting from it the electrical potential measured after flow was stopped. The average of the two corrected potential was taken as the streaming potential.

The zeta potential of the fiber matrix was derived from the streaming potential using the following relationship (J. T. Davis et al., Interfacial Phenomena. Academic Press, New York, 1963):

$$\text{Zeta Potential} = \frac{4\pi\eta}{D} \frac{E_S \lambda}{P}$$

where $\eta$ is the viscosity of the flowing solution, D is its dielectric constant, $\lambda$ is its conductivity, $E_S$ is the streaming potential and P is the pressure drop across the sample during the period of flow. In these tests the quantity $4\pi\eta/DP$ was equal to 0.800.

Porous media in accordance with this invention have positive zeta potentials in aqueous solution at approximately neutral pH. Preferably, they have a positive zeta potential under mildly alkaline conditions, for example, at a pH as high as 9.

The preparation and evaluation of substrates having surface properties controlled by a superstrate imparting a positive charge to the surface of the substrate is described in the Examples below.

While the invention is susceptible to various modifications and alternative forms, certain specific embodiments thereof are described in the examples set forth below. It should be understood, however, that these examples are not intended to limit the invention to the particular embodiments disclosed, but, on the contrary, the intention is to cover all modifications, equivalents, and alternatives falling within the spirit and scope of the invention.

In order that the invention herein described may be more fully understood, the following examples are for illustrative purposes only and are not to be construed as limiting this invention in any manner.

General Procedure for Measuring Surface Area

Measurement of fiber surface area, for example by gas (nitrogen) adsorption—popularly referred to as "BET" measurement—is a useful technique, as the surface area is a direct indication of the extent of fiber surface available to remove heparin. The surface area of melt blown PBT webs can be used to calculate average fiber diameter:

$$\text{Total volume of fiber in 1 gram} = \frac{1}{1.38} \text{ cc}$$

(where 1.38=fiber density of PBT, g/cc)

$$\text{hence } \frac{\pi d^2 L}{4} = \frac{1}{1.38} \quad (1)$$

Area of the fiber is $\pi dL = A_f$ (2)

Dividing (1) by (2), $$\frac{d}{4} = \frac{1}{1.38 A_f} \text{ and } d = \frac{4}{1.38 A_f} = \frac{2.9}{A_f}, \text{ or } (0.345 A_f)^{-1}$$

where L=total length of fiber per gram, d=average fiber diameter in centimeters, and $A_f$=fiber surface area in cm$^2$/g. If the units of d are micrometers, the units of $A_f$ become M$^2$/g (square meters/gram), which will be used hereinafter.

General Procedure for Determining BSA

The Bovine Serum Albumin (BSA) protein absorption test is performed according to a standardized procedure. In this procedure, a solution containing 0.1 mg/ml unlabelled BSA and about 10$^5$ cpm/ml $^{125}$I-labelled BSA was prepared in a phosphate buffered saline (PBS) solution having a pH of 7.2. The PBS solution contained 0.2 grams per liter of monobasic sodium phosphate, 1.2 grams per liter of anhydrous, dibasic sodium phosphate, and 8.77 grams per liter sodium chloride in deionized water.

A sample of a porous test medium was placed in a syringe-type filter holder. Fluid communication between a reservoir holding the BSA test solution and the syringe-type filter was provided by a length of Tygon TM tubing and a peristaltic pump arranged in series. Prior to insertion of a porous test medium sample into the filter holder, the potential nonspecific protein binding sites on both the tubing and the filter holder were blocked by recirculating 1.0 ml of the BSA solution through the tubing and filter holder at a flow rate of 0.3 ml/min for a period of 15 minutes. Following recirculation, the BSA solution was drained from the tubing and filter holder. Residual BSA solution was removed from the tubing and filter holder by circulating about 2.0 ml of PBS through the tubing and filter holder at a flow rate of about 0.3 ml/min for several minutes at ambient temperature.

A 13 mm diameter disc of porous polymeric test medium was placed into the blocked filter holder. The $^{125}$I-BSA solution was then transferred from the ml/min/cm$^2$. The test was continued for a period of 5 minutes, during which time 391 micrograms/cm$^2$ of BSA were transferred to the filter holder. The test medium was then removed from the filter holder and blotted dry on filter paper. The amount of protein (BSA) adsorbed by the membrane disc was determined by radioactive counting in a gamma counter.

General Procedure for Determining CWST

Although the media according to the invention may remain untreated, they are preferably treated to make them even more effective for removing heparin. For example, a medium may be surface modified to increase the critical wetting surface tension (CWST) of the medium. As disclosed in U.S. Pat. No. 4,880,548, the CWST of a porous medium may be determined by individually applying to its surface a series of liquids with surface tensions varying by 2 to 4 dynes/cm and observing the absorption or nonabsorption of each liquid over time. The CWST of a porous medium, in units of dynes/cm, is defined as the mean value of the surface tension of the liquid which is absorbed and that of the liquid of neighboring surface tension which is not absorbed within a predetermined amount of time.

Liquids with surface tensions lower than the CWST of a porous medium will spontaneously wet the medium on contact and, if the medium has through holes, will flow through it readily. Liquids with surface tensions higher than the CWST of the porous medium may not flow at all at low differential pressures and may do so unevenly at sufficiently high differential pressures to force the liquid through the porous medium. In order to achieve adequate priming of a fibrous medium with a liquid such as blood, the fibrous medium preferably has a CWST in the range of about 53 dynes/cm or higher.

General Procedure for Determining Activated Partial Thromboolastin Time

Activated Partial Thromboplastin Time (aPTT) for plasma was determined using the MLA Electra Model 800, a commercial automated instrument designed for measuring clotting time and which is manufactured by Medical Laboratory Automation, Inc. of Pleasantville, N.Y.

The aPTT was performed according to Proctor, et al., *Am. J. Clin. Pathol.*, 36:312 (1961), the procedure recommended by the manufacturer in the operating instructions for the MLA Electra 800. The reagents used in the test were Actin FS Activated PTT Reagent, a product of American Dade division of American Hospital Supply (del Caribe, Inc.), and 0.02M calcium chloride solution, also supplied by American Dade.

EXAMPLES

A web of melt-blown, polybutylene terephthalate fibers having an average fiber diameter of about 2.6 micrometers fibers was used as a substrate in the following examples. The web had a basis weight of 5.2 grams per square foot.

The web was subject to surface modification by radiation grafting by the following steps: Cylindrical rolls of the above-described web, were formed having a diameter of approximately 3 inches and a length of 10 inches and each was then saturated with a monomer solution as set forth in Table 1 (Examples 1 and 2). Prior to contact with the monomer solution, the dry roll of the web was placed in a sealed metal canister and the canister was evacuated. The monomer solution then was admitted and the roll was saturated by backfilling. The saturated roll was then exposed to a dose of gamma radiation as set out in Table 1, to achieve the desired surface modification following which the roll was washed by applying deionized water down through the length of the roll at a rate of about 75 ml per minute for 16 hours. The web was then thoroughly dried in a recirculating air oven in about 3 foot long sheets, at 100° C. for the time specified.

In each example, four layers of the particular surface modified microfiber web were assembled into an injection molded housing having a diameter of 25 millimeters and subjected to the aPtt test for coagulation time, as described earlier. The results for these devices made using the media of Examples 1 and 2 are given in Table 3.

Also, the medium of each Example was tested for BET surface area, CWST, zeta-potential, and BSA protein binding according to the aforementioned procedures. The results for these tests are given in Table 2.

TABLE 1

| Example No. | Monomer 1 (conc.) | Monomer 2 (conc.) | Tertiary Butyl Alcohol (conc.) | Total Dose[3] (MRAD) |
|---|---|---|---|---|
| 1 | Diethylamino ethyl methacrylate (0.3 wt %) | Methyl methacrylate (0.15 wt %) | 6.0 vol %[1] | 0.134 |
| 2 | Trimethyl ammonium ethyl acrylic chloride (4.0 wt %) | Diethylene glycol dimethacrylate (0.5 wt %) | 25.0 vol %[2] | 3.0 |

[1]The monomer solution was prepared by mixing 6 parts by volume of tertiary butyl alcohol with 94 parts by volume water and then adding to this solution 0.3 wt % diethylamino ethyl methacrylate and 0.15 wt % methyl methacrylate based on the tertiary butyl alcohol/water solution which is assumed to have a specific gravity 1.0.
[2]The monomer solution was prepared by mixing 25 parts by volume of tertiary butyl alcohol with 75 parts by volume water and then adding to this solution 4.0 wt % trimethyl ammonium ethyl acrylic chloride and 0.5 wt % diethylene glycol dimethacrylate based on the tertiary butyl alcohol/water solution which is assumed to have a specific gravity 1.0.
[3]The dose rate was 6.7 kilorads/hours for Example 1 and 500 kilorads/hour for Example 2.

TABLE 2

| Example No. | Surface Area ($M^2/g$) | CWST (dynes/cm) | Zeta-Potential (mv/pH) | BSA Binding ($\mu g/cm^2$) |
|---|---|---|---|---|
| 1 | 1.08 | 87 | +23/6.82 | 52 |
| 2 | 1.07 | 93 | +20/9.09 | 118 |
| Control (unmodified) | 1.12 | 51 | −49/6.90 | 126 |

TABLE 3

| | aPTT Time of Filtrate (sec) | | |
|---|---|---|---|
| Device With Medium From Example No. | Plasma Without Heparin | Plasma With 0.4 Total Units of Heparin | Plasma With 1.0 Total Units of Heparin |
| 1 | 29.2 | 32.0 | 64.1 |
| 2 | 32.5 | 33.4 | 31.3 |
| Control (Unfiltered) | 30.8 | 58.0 | No Clot |

Example 1 was dried for 24 hours. Example 2 for 72 hours.

The results in Table 3 clearly demonstrate the ability of products of the present invention to return the clotting time (aPTT) of plasma contaminated with heparin back to its normal value, without undue prolongation of the clotting time of the uncontaminated plasma.

While the invention has been described in some detail by way of illustration and example, it should be understood that the invention is susceptible to various modifications and alternative forms, and is not restricted to the specific embodiments set forth in the Examples. It should be understood, however, that these Examples are not intended to limit the invention but, on the contrary, the intention is to cover all modifications, equivalents, and alternatives falling within the spirit and scope of the invention.

What is claimed is:

1. A method for removing heparin from blood or plasma comprising:
    contacting the blood or plasma with a porous medium having a positively charged surface and being capable of removing heparin from blood or plasma without pH adjustment; and
    removing heparin from the blood or plasma without substantial removal of blood clotting factors.

2. The method of claim 1 wherein the positively charged surface contains amino or ammonium groups.

3. The method of claim 2 wherein the positively charged surface is derived from trimethyl ammonium ethyl acrylic chloride.

4. The method of claim 3 wherein the blood is in an extracorporeal circuit.

5. The method of claim 2 wherein the positively charged surface is derived from diethylamino ethyl methacrylate.

6. The method of claim 5 wherein the blood is in an extracorporeal circuit.

7. The method of claim 1 wherein the positively charged surface contains amino and ammonium groups.

8. The method of claim 1 wherein the positively charged surface contains quaternary ammonium groups.

9. The method of claim 1 wherein the positively charged surface is derived from trimethyl ammonium ethyl acrylic chloride and a polar, non-ionic, ethylenically unsaturated monomer.

10. The method of claim 9 wherein the polar, non-ionic, ethylenically unsaturated monomer is diethylene glycol dimethacrylate.

11. The method of claim 9 wherein the blood is in an extracorporeal circuit.

12. The method of claim 1 wherein the positively charged surface is derived from diethylamino ethyl methacrylate and a polar, non-ionic, ethylenically unsaturated monomer.

13. The method of claim 12 wherein the polar, non-ionic, ethylenically unsaturated monomer is methyl methacrylate.

14. The method of claim 12 wherein the blood is in an extracorporeal circuit.

15. The method of claim 1 wherein the porous medium is a polymeric fibrous matrix, polymeric membrane, or a rigid porous medium.

16. The method of claim 1 wherein the porous medium is a polymer selected from the group consisting of polyolefins, polyesters, and polyamides.

17. The method of claim 16 wherein the porous medium is polybutylene terephthalate.

18. The method of claim 1 wherein the porous medium comprises a substrate selected from the group consisting of polyolefins, polyesters, and polyamides, and at least one superstrate selected from group consisting of
   a) trimethyl ammonium ethyl acrylic chloride;
   b) diethylamino ethyl methacrylate;
   c) "a" and diethylene glycol dimethacrylate; and
   d) "b" and methyl methacrylate.

19. The method of claim 18 wherein the blood is in an extracorporeal circuit.

20. The method of claim 1 wherein the surface area of the medium is in the range from about 0.01 m$^2$/g to about 20 M$^2$/g.

21. The method of claim 20 wherein the surface area of the medium is in the range from about 0.2 M$^2$/g to about 10 M$^2$/g.

22. The method of claim 1 wherein the average residence time is from about 0.1 second to about 50 seconds.

23. The method of claim 1 wherein the porous medium is self-supporting.

24. The method of claim 1 wherein the blood is in an extracorporeal circuit.

25. The method of claim 24 wherein the blood flows through a filter assembly in the extracorporeal circuit at a rate of about 2.5 to about 6 liters/minute.

26. A method for returning the coagulation parameters of a heparin-containing blood or plasma sample to their accurate values comprising passing the sample through a porous medium comprising a substrate and a superstrate, said porous medium having a positively charged surface and being capable of removing heparin from blood or plasma without pH adjustment and without substantial removal of blood clotting factors, thereby removing heparin from the sample.

27. The method of claim 26 wherein the positively charged surface is derived from trimethyl ammonium ethyl acrylic chloride and a polar, non-ionic, ethylenically unsaturated monomer.

28. The method of claim 27 wherein the polar, non-ionic, ethylenically unsaturated monomer is diethylene glycol dimethacrylate.

29. The method of claim 26 wherein the positively charged surface is derived from diethylamino ethyl methacrylate and a polar, non-ionic, ethylenically unsaturated monomer.

30. The method of claim 29 wherein the polar, non-ionic, ethylenically unsaturated monomer is methyl methacrylate.

31. The method of claim 26 wherein the substrate is a polymer selected from the group consisting of polyolefins, polyesters, and polyamides.

32. The method of claim 26 wherein the substrate is polybutylene terephthalate.

33. The method of claim 26 wherein the porous medium comprises a substrate selected from the group consisting of polyolefins, polyesters, and polyamides, and at least one superstrate selected from group consisting of
   a) trimethyl ammonium ethyl acrylic chloride;
   b) diethylamino ethyl methacrylate;
   c) "a" and diethylene glycol dimethacrylate; and
   d) "b" and methyl methacrylate.

34. The method of claim 26 wherein the surface area of the medium is in the range from about 0.01 M$^2$/g to about 20 M$^2$/g.

35. The method of claim 34 wherein the surface area of the medium is in the range from about 0.2 M$^2$/g to about 10 M$^2$/g.

36. The method of claim 26 wherein the average residence time is from about 0.1 second to about 50 seconds.

37. A method for removing heparin from blood or plasma comprising:
   contacting the blood or plasma with a porous medium having a positively charged surface and being capable of removing heparin from blood or plasma without pH adjustment and without substantial removal of blood clotting factors; and
   removing a therapeutically or clinically significant amount of heparin from the blood or plasma.

38. The method of claim 37 wherein the porous medium comprises a substrate selected from the group consisting of polyolefins, polyesters, and polyamides, and at least one superstrate selected from the group consisting of
   a) trimethyl ammonium ethyl acrylic chloride;
   b) diethylamino ethyl methacrylate;
   c) "a" and diethylene glycol dimethacrylate; and
   d) "b" and methyl methacrylate.

39. The method of claim 37 wherein the substrate is a polybutylene terephthalate fiber matrix.

* * * * *